United States Patent [19]

Lai

[11] Patent Number: 5,984,916
[45] Date of Patent: Nov. 16, 1999

[54] OPHTHALMIC SURGICAL LASER AND METHOD

[76] Inventor: Shui T. Lai, 1223 Orchard Glen Cir., Encinitas, Calif. 92024

[21] Appl. No.: 08/051,033

[22] Filed: Apr. 20, 1993

[51] Int. Cl.[6] ..................................................... A61N 5/06
[52] U.S. Cl. ................................ 606/11; 606/3; 606/5; 606/10; 606/13
[58] Field of Search ........................................... 606/2–19

[56] References Cited

U.S. PATENT DOCUMENTS

| | | | |
|---|---|---|---|
| 4,538,608 | 9/1985 | L'Esperance | 606/5 |
| 4,712,543 | 12/1987 | Baron | 606/5 |
| 4,791,927 | 12/1988 | Menger | 606/10 |
| 4,907,586 | 3/1990 | Bille et al. | 606/5 |
| 5,144,630 | 9/1992 | Lin | 372/22 |

*Primary Examiner*—David M. Shay
*Attorney, Agent, or Firm*—Baker & Maxham

[57] ABSTRACT

A laser-based method and apparatus for corneal and intraocular surgery. The preferred method of performing a surface ablation of cornea tissue or other organic materials uses a laser source which has the characteristics of providing a shallow ablation depth or region (about 0.2 $\mu$m to about 5.0 $\mu$m), a low ablation energy density threshold (about 0.2 to 5 $\mu$J/(10 $\mu$m)$^2$), and extremely short laser pulses (having a duration of about 0.01 picoseconds to about 2 picoseconds per pulse) to achieve precise control of tissue removal. The laser beam cross-sectional area is preferably about 10 $\mu$m in diameter. The preferred laser system includes a broad gain bandwidth laser, such as $Ti_3Al_2O_3$, $Cr:LiSrAlF_6$, Nd:YLF, or similar lasers, with a preferred wavelength of about 830 nm, which is generally transmissive in eye tissue. Various surgical procedures can be performed to correct refractive errors or to treat eye diseases. The invention can be used to excise or photoablate regions within the cornea, capsule, lens, vitreoretinal membrane, and other structures within the eye. The invention provides an improved method of eye surgery which has accurate control of tissue removal, flexibility of ablating tissue at any desired location with predetermined ablation depth, an optically smooth finished surface after the surgery, and a gentle surgical beam for laser ablation action.

36 Claims, 9 Drawing Sheets

OPHTHALMIC SURGICAL LASER AND METHOD

BACKGROUND OF THE INVENTION

1. Field of the Invention

This invention relates to methods of, and apparatus for, eye surgery, and more particularly to a laser-based method and apparatus for corneal and intraocular surgery.

2. Related Art

The concept of correcting refractive errors by changing the curvature of the eye was initially implemented by mechanical methods. These mechanical procedures involve removal of a thin layer of tissue from the cornea by a microkeratome, freezing the tissue at the temperature of liquid nitrogen, and re-shaping the tissue in a specially designed lathe. The thin layer of tissue is then re-attached to the eye by suture. The drawback of these methods is the lack of reproducibility and hence a poor predictability of surgical results.

With the advent of lasers, various methods for the correction of refractive errors and for general eye surgery have been attempted, making use of the coherent radiation properties of lasers and the precision of the laser-tissue interaction. A $CO_2$ laser was one of the first to be applied in this field. Peyman, et al., in Ophthalmic Surgery, vol. 11, pp. 325–9, 1980, reported laser burns of various intensity, location, and pattern were produced on rabbit corneas. Recently, Horn, et al., in the Journal of Cataract Refractive Surgery, vol. 16, pp. 611–6, 1990, reported that a curvature change in rabbit corneas had been achieved with a $Co:MgF_2$ laser by applying specific treatment patterns and laser parameters. The ability to produce burns on the cornea by either a $CO_2$ laser or a $CO:MgF_2$ laser relies on the absorption in the tissue of the thermal energy emitted by the laser. Histologic studies of the tissue adjacent to burn sites caused by a $CO_2$ laser reveal extensive damage characterized by a denaturalized zone of 5–10 μm deep and disorganized tissue region extending over 50 μm deep. Such lasers are thus ill-suited to eye surgery.

In U.S. Pat. No. 4,784,135, Blum et al. discloses the use of far-ultraviolet excimer laser radiation of wavelengths less than 200 nm to selectively remove biological materials. The removal process is claimed to be by photoetching without using heat as the etching mechanism. Medical and dental applications for the removal of damaged or unhealthy tissue from bone, removal of skin lesions, and the treatment of decayed teeth are cited. No specific use for eye surgery is suggested, and the indicated etch depth of 150 μm is too great for most eye surgery purposes.

In U.S. Pat. No. 4,718,418, L'Esperance, Jr. discloses the use of a scanning ultraviolet laser to achieve controlled ablative photodecomposition of one or more selected regions of a cornea. According to the disclosure, the laser beam from an excimer laser is reduced in its cross-sectional area, through a combination of optical elements, to a 0.5 mm by 0.5 mm rounded-square beam spot that is scanned over a target by deflectable mirrors. To ablate a corneal tissue surface with such an arrangement, each laser pulse would etch out a square patch of tissue. An etch depth of 14 μm per pulse is taught for the illustrated embodiment. This etch depth would be expected to result in an unacceptable level of eye damage.

Another technique for tissue ablation of the cornea is disclosed in U.S. Pat. No. 4,907,586 to Bille et al. By focusing a laser beam into a small volume of about 25–30 μm in diameter, the peak beam intensity at the laser focal point could reach about $10^{12}$ watts per $cm^2$. At such a peak power level, tissue molecules are "pulled" apart under the strong electric field of the laser light, which causes dielectric breakdown of the material. The conditions of dielectric breakdown and its applications in ophthalmic surgery had been described in the book "YAG Laser Ophthalmic Microsurgery" by Trokel. Transmissive wavelengths near 1.06 μm and a frequency-doubled laser wavelength near 530 nm are typically used for the described method. Near the threshold of the dielectric breakdown, the laser beam energy absorption characteristics of the tissue changes from highly transparent to strongly absorbent. The reaction is very violent, and the effects are widely variable. The amount of tissue removed is a highly non-linear function of the incident beam power. Hence, the tissue removal rate is difficult to control. Additionally, accidental exposure of the endothelium by the laser beam is a constant concern. This method is not optimal for cornea surface or intraocular ablation.

An important issue that is largely overlooked in all the above-cited references is the fact that the eye is a living organism. Like most other organisms, eye tissue reacts to trauma, whether it is inflicted by a knife or a laser beam. Clinical results have shown that a certain degree of haziness develops in most eyes after laser refractive surgery with the systems taught in the prior art. The principal cause of such haziness is believed to be roughness resulting from cavities, grooves, and ridges formed while laser etching. Additionally, clinical studies have indicated that the extent of the haze also depends in part on the depth of the tissue damage, which is characterized by an outer denatured layer around which is a more extended region of disorganized tissue fibers. Another drawback due to a rough corneal surface is related to the healing process after the surgery: clinical studies have confirmed that the degree of haze developed in the cornea correlates with the roughness at the stromal surface.

The prior art also fails to recognize the benefits of ablating eye tissue with a laser beam having a low energy density. A gentle laser beam, one that is capable of operating at a lower energy density for a surgical procedure, will clearly have the advantage of inflicting less trauma to the underlying tissue. The importance of this point can be illustrated by considering the dynamics of the ablation process on a microscopic scale: the ablation process is basically an explosive event. During ablation, organic materials are broken into their smaller sub-units, which cumulate a large amount of kinetic energy and are ejected away from the laser interaction point at a supersonic velocity. The tissue around the ablated region absorbs the recoil forces from such ejections. The tissue is further damaged by acoustic shock from the expansion of the superheated plasma generated at the laser interaction point. Accordingly, a shallower etch depth or smaller etch volumes involves less ejected mass and acoustic shock, and hence reduces trauma to the eye.

It is therefore desirable to have a method and apparatus for performing eye surgery that overcomes the limitations of the prior art. In particular, it is desirable to provide an improved method of eye surgery which has accurate control of tissue removal, flexibility of ablating tissue at any desired location with predetermined ablation depth or volume, an optically smooth finished surface after the surgery, and a gentle surgical beam for laser ablation action.

The present invention provides such a method and apparatus.

SUMMARY OF THE INVENTION

The present invention recognizes that an optically smooth corneal surface and a clear intraocular light path (including post-operative clarity) are all critical to successful ophthalmic surgery. The effects of eye surgery on all of the intraocular elements encountered by light traversing the optical path from the cornea to the retina must be considered. The invention was developed with a particular view to preserving these characteristics.

The preferred method of performing a surface ablation of cornea tissue or other organic materials uses a laser source which has the characteristics of providing a shallow ablation depth or region (about 0.2 $\mu$m to about 5.0 $\mu$m), a low ablation energy density threshold (about 0.2 to 5 $\mu$J/(10 $\mu$m)$^2$) and extremely short laser pulses (having a duration of about 0.01 picoseconds to about 2 picoseconds per pulse) to achieve precise control of tissue removal. The laser beam cross-sectional area is preferably about 10 $\mu$m in diameter.

The preferred laser system includes a broad gain bandwidth laser, such as Ti$^3$.Al$_2$O$_3$, Cr:LiSrAlF$_6$, Nd:YLF, or similar lasers, with a preferred wavelength of about 400 nm to about 1900 nm, which is generally transmissive in eye tissue.

Each laser pulse is directed to its intended location in or on the eye through a laser beam control means, such as the type described in a co-pending, commonly-owned patent application for an invention entitled "Method of, and Apparatus for, Surgery of the Cornea" (U.S. patent application Ser. No. 07/788,424).

Various surgical procedures can be performed to correct refractive errors or to treat eye diseases. The surgical beam can be directed to remove cornea tissue in a predetermined amount and at a predetermined location such that the cumulative effect is to remove defective or non-defective tissue, or to change the curvature of the cornea to achieve improved visual acuity. Excisions on the cornea can be make in any predetermined length and depth, and in straight line or in curved patterns. Alternatively, circumcisions of tissue can be made to remove an extended area, as in a cornea transplant. The invention can be used to excise or photoablate regions within the cornea, capsule, lens, vitreoretinal membrane, and other structures within the eye.

The present invention provides an improved method of eye surgery which has accurate control of tissue removal, flexibility of ablating tissue at any desired location with predetermined ablation depth, an optically smooth finished surface after the surgery, and a gentle surgical beam for laser ablation action.

The details of the preferred embodiments of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings refer to like elements.

DETAILED DESCRIPTION OF THE INVENTION

Figure 1A:
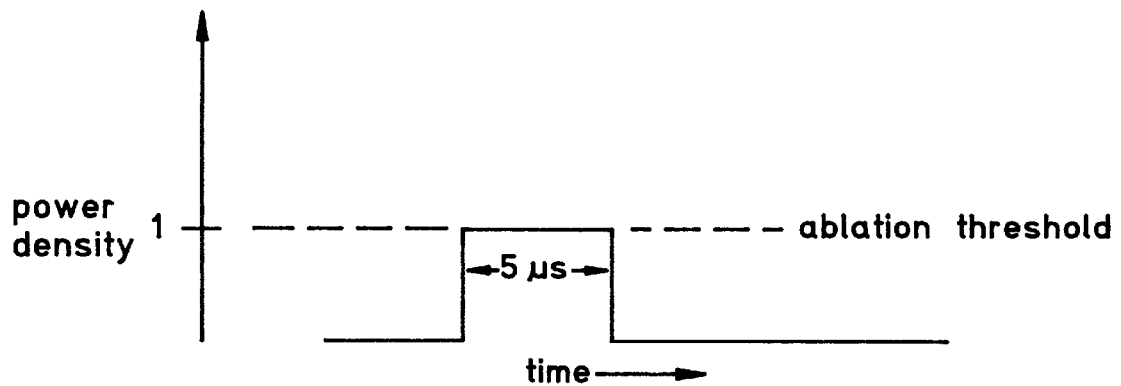
FIG. 1A is a diagram showing the power density of a square laser pulse versus time for a 5 ns pulse.

Throughout this description, the preferred embodiment and examples shown should be considered as exemplars, rather than limitations on the method and apparatus of the present invention.

The laser apparatus and method disclosed in this invention is for achieving two principal objectives:

(1) The damage zone around the material ablated by the inventive laser system must be substantially reduced in comparison to prior art laser systems.

(2) For each laser pulse deposited in or on the eye, a definite predetermined depth or volume of tissue is to be ablated. The ablated depth per laser pulse must be controllable and about 5 $\mu$m or less, and preferably about 0.5 $\mu$m or less.

To achieve these objectives, the present invention uses short duration laser pulses from about 0.01 to 2 picoseconds to reduce inflicted damage to target tissues. The preferred laser system includes a Ti$^3$.Al$_2$O$_3$, Cr:LiSrAlF$_6$, Nd:YLF, or similar laser with a preferred wavelength of about 400 nm to about 1900 nm. The laser beam cross-sectional area is preferably about 10 $\mu$m in diameter. The importance of these characteristics is explained below.

Laser Pulse Duration

A fundamental problem of prior art ophthalmic surgical laser systems is that such systems fail to adequately take into account the interaction of the laser beam with organic tissue in the ablation process, particularly when using relatively transmissive laser wavelengths. Laser ablation occurs when the laser beam intensity, or energy level, is increased beyond a certain threshold level, causing dielectric breakdown. However, the actual ablation conditions vary depending on the characteristics of a wide range of laser parameters and the composition of the material to be ablated. When laser energy is absorbed in an organic material, on the most basic level, the electronic configuration of the target polymer molecules makes a transition to one of its excited electronic states. Each polymer is made of hundreds or more of sub-units of smaller molecules called monomers. The monomers are made of even smaller units of radicals consisting of combinations of hydrogen, carbon, oxygen, and nitrogen atoms. Depending on the energy level of the laser photons, a polymer can be broken into constituent monomers, radicals, or ionized atoms.

For a laser having a wavelength near about 830 nm, a single laser photon is not sufficiently energetic to break any molecular bond. Breaking such a bond is a highly non-linear multi-photon process. After absorbing an initial photon, a molecule is promoted to an excited electronic state configuration, with its electrons in higher energy orbits. This state will decay, or "relax", if additional photons are not absorbed to maintain the excited electronic state configuration.

As the laser beam intensity increases further towards the ablation threshold, additional photons are absorbed, and the excited electron density reaches a critical volume density such that the electronic orbitals can pair and transfer the sum of their energy to a single electron orbital. This process breaks the molecule into two or more pieces, and releases an energetic electron. At this point, the organic medium is damaged but not yet ablated.

With increased power levels of the laser beam, further photons are absorbed, and the excited electron density increases correspondingly. At the same time, the excited electrons migrate down the polymeric chain of the organic material, and spread towards the bulk volume with lower excited state density. The present invention recognizes that the excited state electronic orbitals are the means for energy storage that will eventually fuel the ablation process, and the electronic energy state migration process plays a key role in the dynamics controlling the initiation of the laser ablation. Because photoablation requires multiple photons interacting with organic tissue molecules, "ignition" of ablative action near the threshold condition is determined by a statistical process. That is, determination of the average etch depth or volume for laser beam energies near the ablation energy threshold are derived by measuring actual etch depth or volume after hundreds or sometimes thousands of laser pulses over the same location, and determining an average etch amount per pulse. On a single shot basis, however, the etch depth or volume could vary significantly, and most of the laser pulses may not ablate any material at all. In general, the ablation threshold for a particular wavelength is the total integrated energy required for 50% of laser pulses to have an effect.

Because of the statistical nature of laser pulse ablation, it is important to note that a reproducible etch depth or volume will not necessarily be attained at reduced levels of laser energy per pulse, especially when the energy level is close to being at an arbitrarily small value above the ablation energy threshold. Thus, in order to ensure a reliable etch depth or etch volume for each single laser pulse, the operating energy per pulse is conventionally set at a multiple of the ablation energy threshold level; a factor of 3 to 4 times the ablation energy threshold is usually considered sufficient to achieve satisfactory results. For an excimer laser, the ablation threshold level is at about 50 mJ/cm$^2$; basically no ablative action is observed at a laser energy density below this threshold level. Accordingly, the typical energy density in an excimer surgical laser beam required for cornea ablation is about 150–250 mJ/cm$^2$.

Consider now the geometric distribution of the excited state orbitals in an organic material. As the laser light is absorbed in the organic material, by Beer's law, the front surface where the material is first exposed encounters most of the laser photons, and the beam intensity decreases exponentially as it traverses deeper into the material. Hence, the spatial distribution of the excited state density also decreases accordingly, characteristic of the absorption coefficient of the material at the laser wavelength. It follows that the slope of the distribution curve of the excited state electron density is directly related to the absorption coefficient. Additionally, the steeper the slope of the excited state density distribution curve, the more spatially localized is the excited state density.

Thus, to maintain a small laser beam interaction point (e.g., about 1 $\mu$m to about 30 $\mu$m, and preferably about 10 $\mu$m), the slope of the excited state density distribution curve must be steep. To obtain a steep slope, the pulse width of the impinging laser beam should be kept narrow.

Figure 1B:
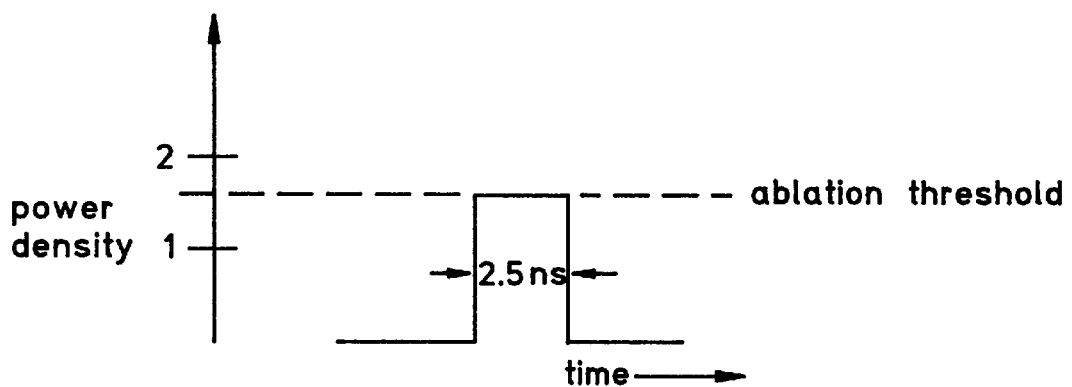
FIG. 1B is a diagram showing the power density of a square laser pulse versus time for a 2.5 ns pulse.

It is known that if ablation is found to occur at a particular laser peak power, narrowing the laser pulse increases the ablation threshold. For example, FIG. 1A is a diagram showing the power density of a square laser pulse versus time for a 5 ns pulse. If the ablation threshold is found to occur at a particular power density (arbitrarily considered to have a value of "1" in FIG. 1), then a higher ablation threshold is required when the pulse is narrowed. That is, the total integrated energy of the shorter laser pulse must approach the total integrated energy of the longer laser pulse. However, it is also known that halving the pulse duration does not require a doubling of the power density of the pulse. For example, FIG. 1B is a diagram showing the power density of a square laser pulse versus time for a 2.5 ns pulse. The ablation threshold is less than twice the ablation threshold of a 5 ns pulse.

Empirical results obtained from materials damage indicate that a particular ablation threshold can be reached with a pulsed laser beam 100 times shorter in duration than a longer duration pulse when the total integrated energy of the shorter laser pulse is at about 10% of the total integrated energy of the longer pulse.

Figure 2:
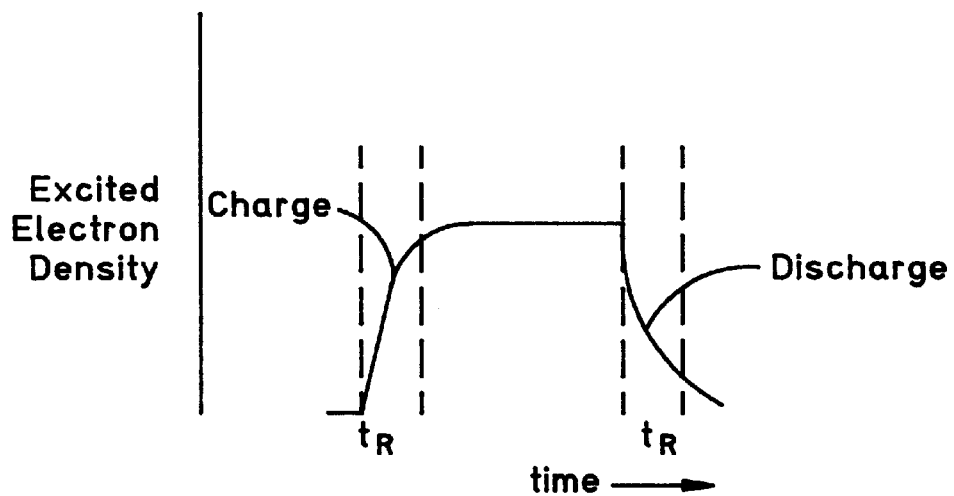
FIG. 2 is a diagram showing the excited state electron density of eye tissue at a laser beam interaction point.

Conventional teaching requires an increase in the ablation threshold energy density as pulse widths are decreased. However, it has been recognized in the present invention that the reason halving the pulse width of a laser does not require a doubling of the ablation threshold energy density is related to the build-up and relaxation of the excited state electron density. FIG. 2 is a diagram showing the excited state electron density of eye tissue at a laser beam interaction point. The diagram shows that the excited state electron density is related to the energy density of the incident laser beam. As photons from a laser beam interact with tissue, the electron state of the molecules undergo "charging" to a steady state. The "charging" time $t_R$ is related to the electron migration rate. The discharge time is also equal to $t_R$. The charge/discharge time $t_R$ is approximately 0.5 to 1 picoseconds.

After the initial photons of a laser pulse charge the excited state electron density to a steady state, the remaining photons of the pulse have essentially no effect on such density. The steady state arises because energy migrates away from the beam interaction point. When using longer duration pulses, the energy migration process is counter-balanced by additional laser beam pumping to build up the critical excited state electron density. However, with a longer laser pulse, the excited state orbitals diffuse from the laser interaction point into the depth of the material (along the laser beam direction). Hence, the excited state distribution curve will have less steep a slope compared to the curve from a shorter pulse. The present invention recognizes that the depth of the tissue layer which has sufficient excited state orbitals to satisfy the ablation threshold condition will be correspondingly deepened. Therefore, the damage inflicted by a longer duration laser pulse is more extensive than the damage inflicted with a shorter duration pulse.

As noted above, for a laser pulse having a low energy density, a longer pulse duration is required to achieve sufficient photon interactions to charge the excited state electron density to a steady state. Conversely, for a laser pulse having a shorter duration, a higher energy density is required. However, because of the higher energy density, more photon interactions per unit of time occur, thereby more rapidly charging the excited state electron density to the steady state. Less energy migrates away from the laser interaction point. Consequently, the total integrated energy of a narrower pulse need not be as great as the total integrated energy of a longer pulse to achieve the ablation threshold.

Figure 1C:
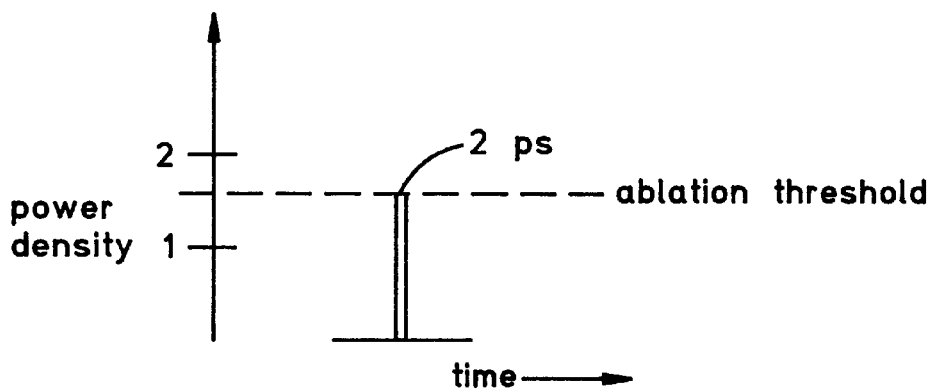
FIG. 1C is a diagram showing the power density of a square laser pulse versus time for a 2 ps pulse.
Figure 3:
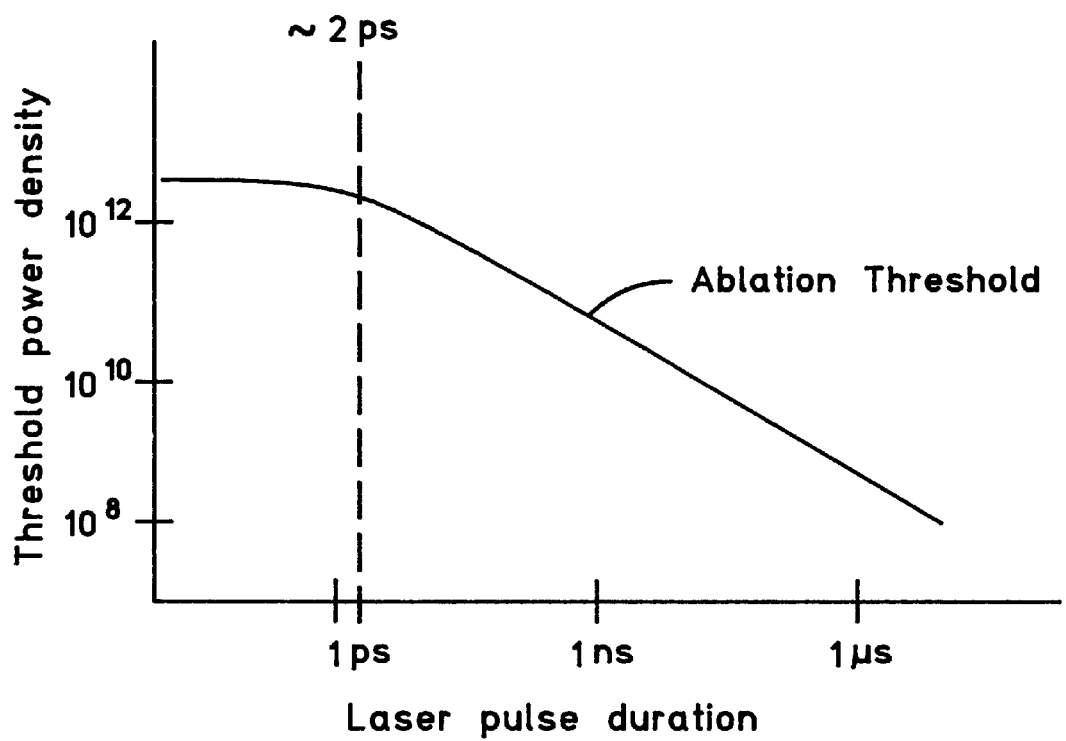
FIG. 3 is a diagram showing eye tissue ablation energy threshold versus pulse width.

Importantly, it has been discovered in the present invention that the power density for the ablation threshold reaches an approximately constant level as the laser pulse width decreases and closely approaches the charge/discharge time $t_R$. For example, as shown in FIG. 1C, a 2 picosecond pulse may have about the same ablation threshold as a much shorter pulse. FIG. 3 is a diagram showing eye tissue ablation energy threshold versus pulse width. As the laser pulse width reaches about 2 picoseconds, and the energy density of the beam is about $1.0 \ \mu J/(10 \ \mu m)^2$ for an 830 nm wavelength, the number of photons is sufficient to maintain a steady state excited state electron density without significant decay. This relationship between pulse duration and constant ablation threshold has been found to exist from about 2 picoseconds down to at least 0.01 picoseconds.

Thus, ablation can be achieved at a low ablation threshold energy using such extremely short duration laser pulses. Further, tissue damage from acoustic shock and kinetic action from dissociated matter is directly proportional to energy deposited at the laser interaction point. If the ablation threshold is achieved at less than the total pulse energy, the remaining energy in the pulse is completely absorbed by the generated plasma, thereby contributing to the explosive effect of the tissue ablation. Both acoustic shock and kinetic action are decreased by reducing the pulse duration.

Figure 4:
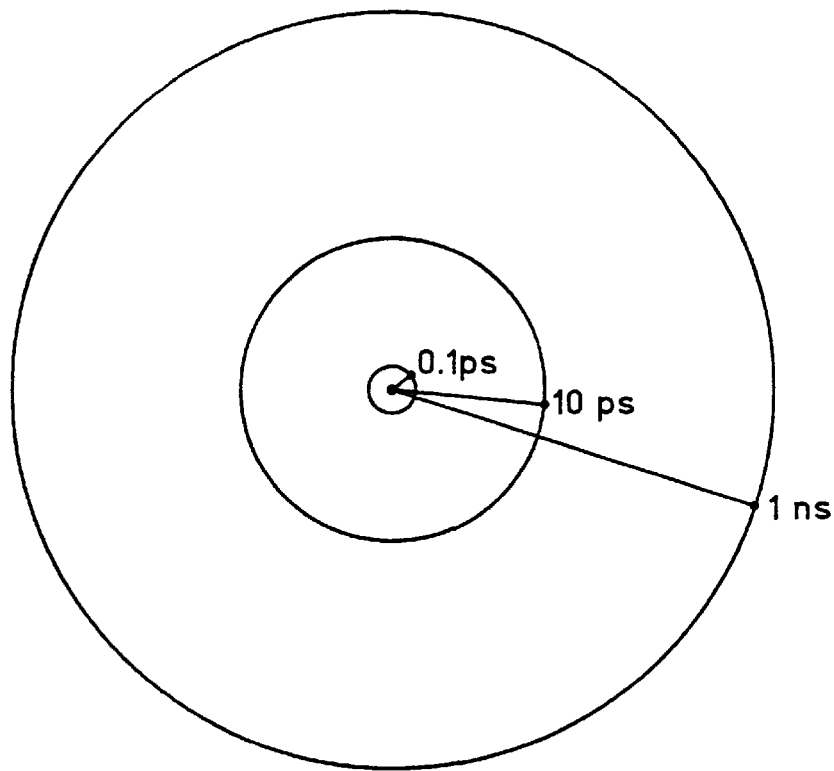
FIG. 4 is a diagram showing the relative diameters of tissue regions removed by laser pulses at the ablation threshold for pulses of approximately 1 ns, 10 ps, and 1 ps duration.

Another benefit from reducing the pulse duration is limitation of damage to tissue surrounding the laser interaction point due to energy migration. FIG. 4 is a diagram showing the relative diameters of tissue regions removed by laser pulses at the ablation threshold for pulses of approximately 1 nanosecond, 10 picoseconds, and 0.1 picosecond duration. As can be seen, the range of tissue removal and surrounding tissue damage is substantially less for the shorter pulses (the volume of tissue removed is proportional to energy deposited, which falls off from the center of the interaction point proportionally to the radius cubed).

Transmissive Wavelengths

In order to perform intraocular surgical procedures, the laser beam necessarily must pass through overlying tissue to the desired location without damage to the overlying tissue. Accordingly, the illustrated embodiment of the present invention uses an 830 nm wavelength for the laser beam, which is generally transmissive in eye tissue. Such a wavelength can be generated in known fashion from a broad gain bandwidth (i.e., $\Delta\lambda > ~1$ mm) laser, such as a $Ti^3.Al_2O_3$, $Cr:LiSrAlF_6$, Nd:YLF, or similar laser. One such laser is described in co-pending U.S. patent application Ser. No. 07/740,004, filed Aug. 2, 1991, entitled "Two Dimensional Scanner-Amplifier Laser" and assigned to the assignee of the present invention.

Other wavelengths could be used as desired, since absorption and transmission in the eye is a matter of degree. Thus, less transmissive wavelengths can be used for procedures at or near the front of the eye, such as the cornea. In general, acceptable wavelengths include the ranges of about 400 nm to about 1900 nm, about 2.1 $\mu$m to about 2.8 $\mu$m, and longer than about 3.1 $\mu$m.

Figure 5:
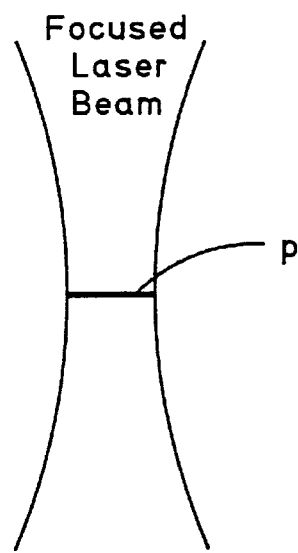
FIG. 5 is a diagram showing the interaction point of a laser beam.

Because of the preferred transmissivity of the laser beam, and the requirement that a threshold energy density be achieved to ignite ablation, the interaction "point" (it is actually a generally planar region) of the laser beam can be focused quite tightly. FIG. 5 is a diagram showing the interaction point P of a laser beam. The portion of the beam above and below the interaction point P lacks sufficient energy density to ignite photoablation. Hence, those portions of the laser beam pass through the surrounding tissue without causing damage. Where the beam is focused most tightly (i.e., the focal point), the energy density is sufficient to initiate ablation.

Size of the Laser Interaction Point

Another way to reduce the shock to the eye is by using a smaller beam area at the interaction point to reduce the integrated recoil forces. Consequently, the laser beam cross-sectional area of the invention at the interaction point is preferably about 10 $\mu$m in diameter. The preferred beam size of the invention contrasts with current excimer laser surgical systems, which subject an ablation zone to a surgical beam that is typically 4–6 mm in diameter.

The beam diameter can be varied to any tolerably achievable smaller or larger dimension, as required by the particular type of surgery. In particular, a range of about 1 $\mu$m to about 30 $\mu$m is preferred.

The Inventive Apparatus

Figure 6:
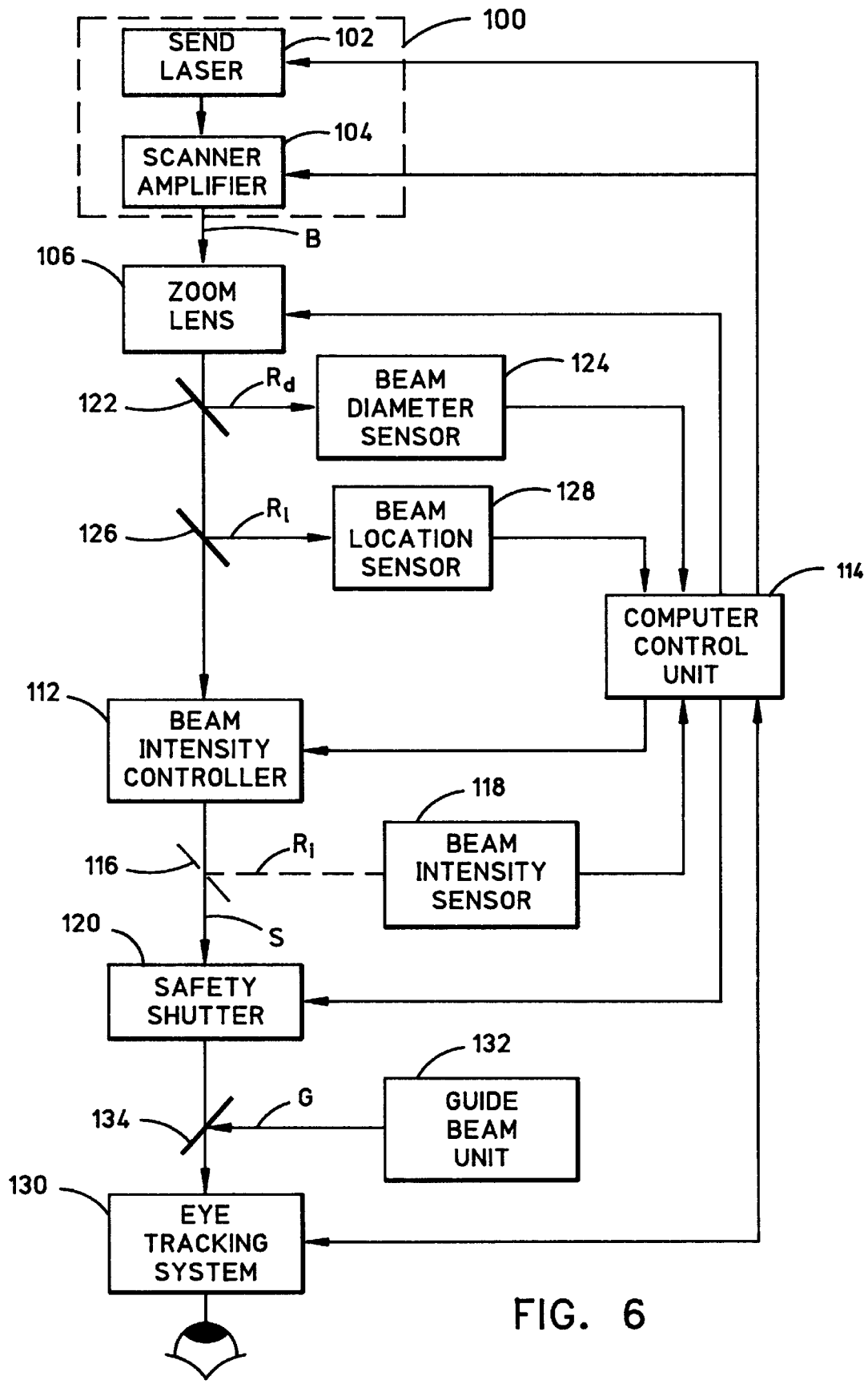
FIG. 6 is a block diagram of the preferred embodiment of the inventive apparatus.

Each laser pulse of the type described above is preferably directed to its intended location in or on the eye through a laser beam control means, such as the type described in the co-pending, commonly-owned U.S. patent application Ser. No. 07/788,424. FIG. 6 shows a block diagram of such a laser and control system.

More particularly, FIG. 6 shows a laser unit 100 for generating an initial laser beam B. The laser unit 100 is of the type that can outputs a beam rapidly deflectable or scannable under electronic control in two dimensions to any location in an area defined by orthogonal X and Y axes. One such laser unit is described in detail in the co-pending, commonly-owned patent application for invention entitled "Two Dimensional Scanner-Amplifier Laser" (U.S. patent application Ser. No. 07/740,004), which is hereby incorporated by reference.

The initial laser beam B comprises a sequence of laser pulses having a pulse repetition rate of about 100 to 100,000 pulses per second. The actual number of laser pulses used for a surgery is determined by the amount of tissue to be removed. In a preferred embodiment, the laser unit 100 includes a seed laser 102 and a scanner-amplifier laser 104. Preferably, the laser media in both the seed laser 102 and the scanner-amplifier 104 is a Ti:$Al_2O_3$ solid state laser crystal.

After emerging from the laser unit 100, the laser beam B passes through a computer-controllable, motorized zoom lens 106, which provides control over the diameter of the laser beam B. In practice, the zoom lens 106 may be placed in a number of suitable positions along the optical path of the laser beam between the laser unit 100 and a target. The motor actuation of the zoom lens 106 may be by any known means, such as electrical gear drives or piezoelectric actuators.

While the laser beam B could be used directly for surgical purposes, in the preferred embodiment, the entire surgical laser apparatus includes a number of control and safety systems. In particular, the present invention includes means for monitoring and controlling the intensity of the beam, means for blocking the surgical beam in the event of a malfunction, means for monitoring and controlling the laser beam diameter and intensity profile, and means for verifying the two-dimensional (X-Y) scan position of the surgical beam.

Referring again to FIG. 6, the laser beam B passes through a beam intensity controller 112, the output of which is the surgical laser beam S. The beam intensity controller 112 permits regulation of the energy of each laser pulse so that the etch depth of each pulse may be precisely controlled. In the preferred embodiment, the beam intensity controller 112 is an electro-optical filter, such as an electrically activated Pockels cell in combination with an adjacent polarizing filter.

In the preferred embodiment, the beam intensity controller 112 is coupled to a computer control unit 114, which is suitably programmed to vary the intensity of the output surgical laser beam S as required for a particular surgical procedure. The degree of beam retardation as a function of applied electrical signal can be ascertained by standard calibration techniques. The preferred location of the beam intensity control unit 112 is as shown in FIG. 6. However, the beam intensity control unit 112 can be placed at several suitable locations in the beam path between the laser unit 100 and a target. In the preferred embodiment, the intensity of the surgical beam S is regulated to have an ablation energy density of less than or equal to about $5 \mu J/(10 \mu m)^2$.

The present invention optionally provides for positive feed-back measurement of the beam intensity. A partially transmissive beam-splitting mirror 116 is placed after the beam intensity controller 112, and the reflected beam $R_i$ is directed to a beam intensity sensor 118. The beam intensity sensor 118 may be simply a photocell, although other elements, such as focussing optics, may be included. By monitoring the electrical output of the beam intensity sensor 118 with the computer control unit 114, the intensity of the surgical laser beam S can be positively measured to verify the proper operation of the beam intensity controller 112. The output of the beam intensity sensor 118 as a function of intensity of the surgical laser beam S can be ascertained by standard calibration techniques.

The inventive system also preferably includes a safety shutter 120, which is coupled to the computer control unit 114. The safety shutter 120 may be, for example, a mechanically-actuated shutter operated in a "tail-safe" mode. For example, the safety shutter 120 may include a solenoid-actuated shield that is positively held open by application of electrical energy to the solenoid. Upon command of the computer control unit 114, or failure of the entire system, electrical energy to the solenoid is cut off, causing the solenoid to retract the shield into position to block the path of the surgical laser beam S. The safety shutter 120 is also useful for temporarily blocking the laser beam S while changing the position of the patient's eye or of the beam itself, without turning the laser beam S completely off.

In an alternative embodiment, the safety shutter 120 may include a Pockels cell and polarizer configured as a light valve, with the Pockels cell biased with respect to the polarizer by application of an electrical voltage such that maximum light is normally transmitted by the combination. Cessation of the applied voltage will cause the output of the Pockels cell to become polarized orthogonal to the transmission direction of the polarizer, hence blocking the surgical laser beam S. Using this alternative configuration, the safety shutter 120 and the beam intensity controller 112 may be combined into a single unit.

Any other suitable means for quickly blocking the surgical laser beam S on command or in the event of system failure may be used to implement the safety shutter 120. In practice, the safety shutter 120 may be placed in a number of suitable positions along the optical path of the laser beam between the laser unit 100 and a target.

To control beam diameter, the inventive system provides a partially transmissive beam-splitting mirror 122 that reflects part of the beam $R_d$ to a beam diameter sensor 124. In practice, the beam diameter sensor 124 may be placed in a number of suitable positions along the optical path of the laser beam between the laser unit 100 and a target. The beam diameter sensor 124 preferably includes at least a diverging (concave) lens and a converging (convex) lens configured as a magnifying telescope (i.e., the two lenses have a common focal point, with the focal length $f_2$ of the converging lens being greater than the focal length $f_1$ of the diverging lens, and having optical centers aligned with the incident laser beam in its un-deflected position). The incident beam $R_d$ enters the diverging lens and exits the converging lens. Such a configuration of lenses, while enlarging the incident beam, will also reduce the scan angle of the exiting beam.

The resulting enlarged beam is directed to a high sensitivity, low contrast imaging device, such as a charge-coupled device (CCD) camera. The converging and diverging lenses are chosen to expand the incident beam $R_d$ so that the largest possible diameter for the beam just fits within the imaging device. In the preferred embodiment, the size of the beam is determined by periodically addressing a central row and a central column of the imaging device and counting the number of pixels on each sampled axis that have been illuminated. By comparing the diameter of the beam in both the X and Y directions, the beam diameter sensor can determine whether the incident laser beam B is approximately circular and has the desired diameter.

The beam diameter sensor 124 can also be used to determine the intensity profile of the laser pulses, since each pixel in the beam diameter sensor 124 can generate an output indicative of the intensity of light incident to the pixel. By comparing pixel values from radially symmetric points in the pixel array, it can be determined if an incident laser pulse or series of pulses has the desired radially symmetric intensity profile, or if the pulses have developed "hot spots" of out-range intensity values.

The output of the beam diameter sensor 124 is coupled to the computer control unit 114. The computer control unit 114 is in turn coupled to the motorized zoom lens 106, which provides control over the diameter of the laser beam B. The computer control unit 114 is suitably programmed to vary the diameter of the laser beam as required for a particular surgical procedure. The output of the beam diameter sensor 124 as a function of beam diameter can be ascertained by standard calibration techniques.

This configuration provides positive feed-back of the beam diameter emanating from the laser unit 100. If the beam diameter sensor 124 detects an out-of-range beam (either diameter or intensity profile), the computer control unit 114 can take appropriate action, including activation of the safety shutter 120.

To verify the X-Y scan position of the laser beam, the inventive system provides a partially transmissive beam-splitting mirror 126 that reflects part of the beam energy $R_i$ to a beam location sensor 128. The beam location sensor 128 preferably includes at least a converging (convex) lens and a diverging (concave) lens configured as a reducing telescope (i.e., the two lenses have a common focal point, with the focal length $f_2$ of the diverging lens being greater than the focal length $f_1$ of the converging lens, and having optical centers aligned with the incident laser beam in its un-deflected position). The incident beam $R_i$ enters the converging lens and exits the diverging lens. Such a configuration of lenses, while reducing the incident beam, will also increase the scan angle of the exiting beam.

The resulting increased-scan angle beam is directed to a silicon photo-detector, such as the position sensing detector, model DLS-20 manufactured by UDT Sensors, Inc. of Hawthorne, Calif. The photo-detector provides a voltage reading with respect to the two-dimensional (X-Y) position of an illuminating spot at the detector surface. The output of the beam location sensor 128 is coupled to the computer control unit 114. Calibration of the voltage reading generated from the un-deflected incident beam position on the photo-detector will indicate the origin of the laser beam in the XY-scan plane. Any deflection of the beam from the origin will generate voltage readings indicative of the spot on the photo-detector surface illuminated by the laser beam. These voltage readings are calibrated against the indicated location of the surgical beam as set by the computer control unit 114. During operation, the output of the beam location sensor 128 would be sampled periodically (for example, about 1,000 times per second) and compared to a prepared calibration table in the computer control unit 114 to determine if the actual beam position matches the indicated position.

This configuration provides positive feed-back of the beam position emanating from the laser unit 100. If the beam location sensor 128 detects an out-of-position beam, the computer control unit 114 can take appropriate action, including activation of the safety shutter 120.

Thus, the preferred embodiment of the inventive surgical laser apparatus provides for safe and effective surgery by continuously monitoring all aspects of the condition of the surgical laser beam S, including beam intensity, diameter, and X-Y scan position.

In order to provide accurate positioning of the surgical laser beam S, an eye tracking system 130 is placed in the path of the surgical laser beam S, preferably in close proximity to a target eye. The eye tracking system 130 monitors movement of a patient's eye and adjusts the position of the surgical laser beam S to compensate. Such tracking may be accomplished by providing fiducial marks on the eye and optically tracking movement of said fiducial marks. Deflectable mirrors may then be used to steer the surgical laser beam S. An example of one such system is described in co-pending U.S. patent application Ser. No. 07/788,424, which description is hereby incorporated by reference.

In order to improve the ease of use of the present invention, and to ensure proper alignment of the surgical laser beam S with respect to a target eye, the present invention includes a guide beam unit 132. The guide beam unit 132 includes a low-power laser with an output of preferably less than 1 milliwatt at initial output and preferably attenuated to the microwatt level for safe usage for direct viewing. The low-power laser generates a guide beam which is conditioned optically so that it is aligned with the surgical laser beam S and can be used as a indicator of the location of the surgical laser beam S. Additionally, the guide beam can be used as an element for the alignment of a patient's eye in preparation for surgical procedures.

Example Surgical Procedures

The laser surgical system of the present invention can perform numerous types of surgical procedures on the eye. Before the initiation of a surgical procedure, the focal point of the surgical laser beam S is placed a known reference location, preferably in the vicinity of the point of surgery. After adjustment of the target tissue location, such as by use of a guide beam, and at the satisfaction of the surgeon, the eye tracking system 130 is activated. Any eye movement thereafter will be compensated for by a corresponding automatic adjustment of the laser beam position.

According to the prescription of the surgeon, the inventive system can perform any and all of the following procedures: (1) The inventive system can easily create straight line and curved-line excisions, of any predetermined length and depth, at any location determined by a surgeon.

Figure 7:
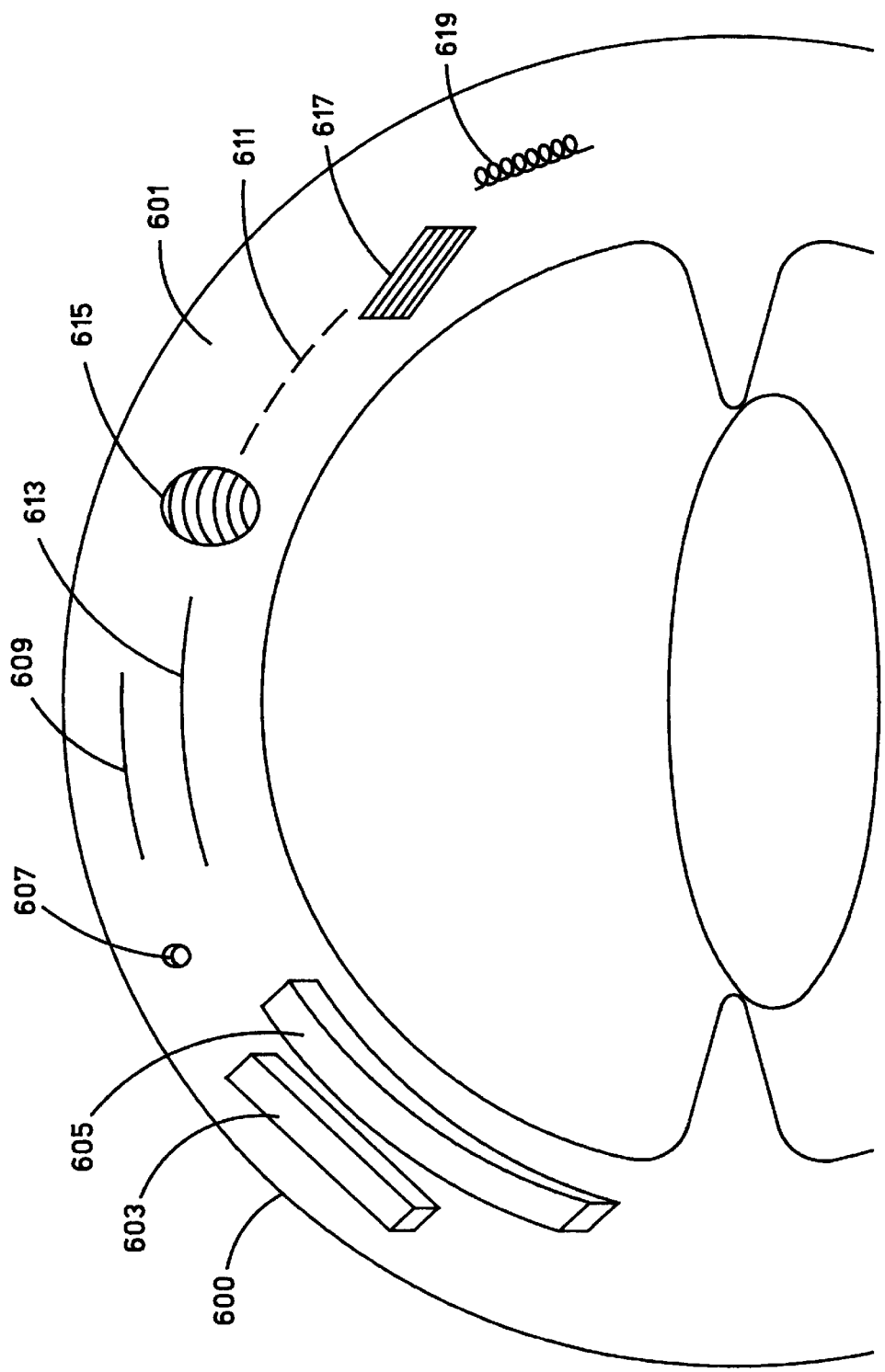
FIG. 7 is a cross-sectional side view of a cornea showing some of the resulting incisions which can be formed in a stroma by the present invention.

FIG. 7 illustrates some of the resulting excisions which can be formed in the stroma 601 of an eye 600. The excisions shown in FIG. 7 are merely intended to illustrate a limited number of examples of the types of excisions that can be made using the invention, and are not intended to demonstrate any particular surgical procedure, or to imply that the illustrated excisions are the only relevant types of excisions that can be easily made in accordance with the present invention. The excisions illustrated in FIG. 7 include a straight channel 603, a curved channel 605, a point 607, a line 609, an interrupted line 611, a curve of varying depth 613, a circular area 615, a square or parallelepiped area 617, or a spiral 619. The invention encompasses any combination of such excisions.

Figure 8B:
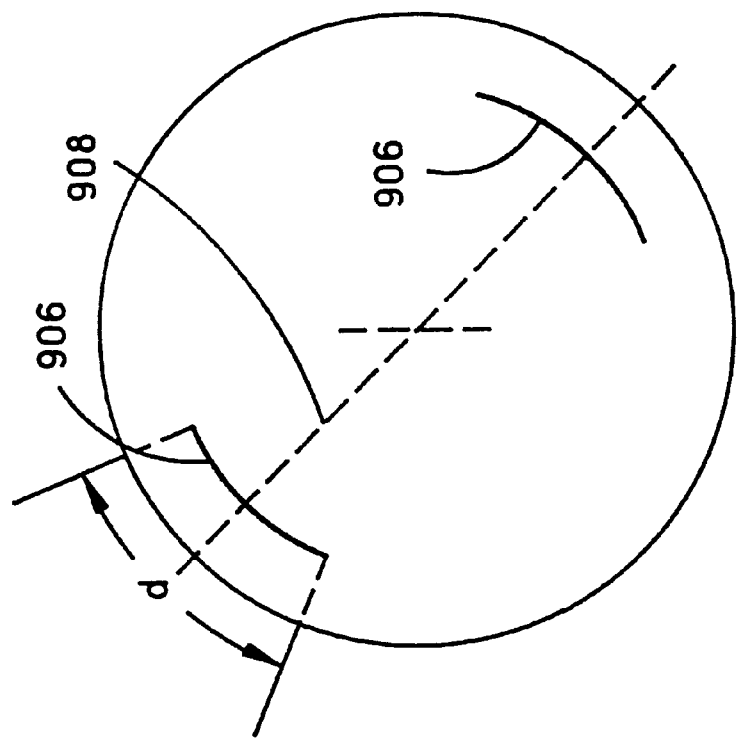
FIG. 8B is a top view of a cornea, showing the use of the present invention to make transverse-cut excisions on the cornea.
Figure 8A:
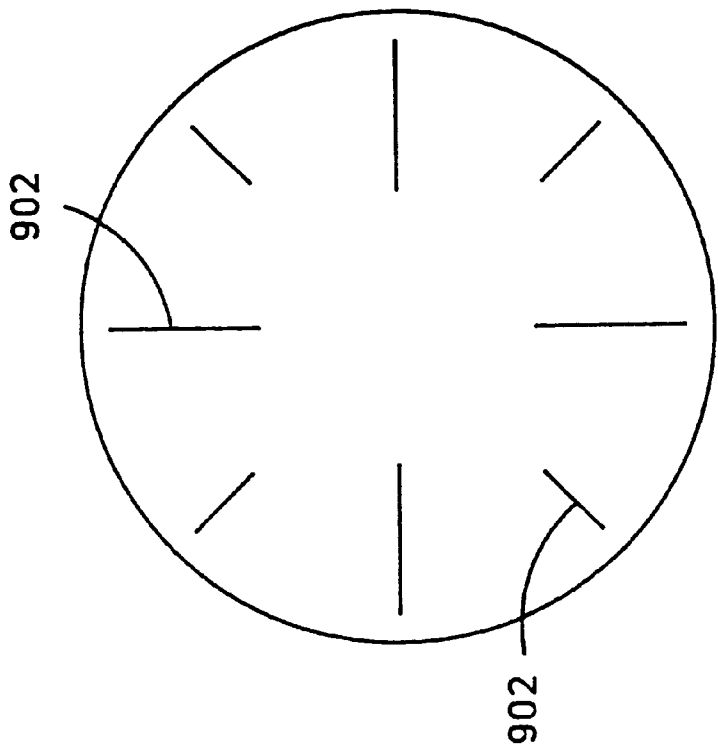
FIG. 8A is a top view of a cornea, showing the use of the present invention to make radial excisions on the cornea.

As illustrated in FIG. 8A, multiple radial cuts 902, equal or partially equal in excision length and with an angular separation between cuts, can be made on the cornea with the present surgical system. An excision can be made by directing the surgical laser beam S to a predetermined location at the cornea, and removing the desired amount of tissue by controlling the laser beam energy dosage. The present invention provides options for making an excision with either a wide excision width by using a larger beam spot size on the cornea surface, or a fine excision by using a more focussed beam spot. With the present invention, the depth of each cut can be varied over the length of a predetermined excision.

The invention can also easily generate arcuate cuts or transverse cuts ("T-cuts"), as shown in FIG. 8B. By directing the surgical laser beam S to make a pair of opposing curved excisions 906 along an axis 908 relative to the center of the eye, the refractive power of eye is decreased along the axis.

The exact length d and the location of the excision can vary according to the amount of desired correction, in known fashion.

In general, excisions in the cornea can be made at effective locations for performing radial keratotomies or making T-cuts or arcuate cuts, to correct myopia, hyperopia, or astigmatism (regular or irregular).

The inventive system can also be used for procedures in cornea transplants. A circumcision of the cornea in any predetermined shape (e.g., circular, elliptical, polygonal, etc.) can be performed on the donor eye and the recipient's eye. In both cases, a computer control unit 114 (see FIG. 6), as described in the co-pending U.S. patent application Ser. No. 07/788,424, calculates the beam location based on the particular shape excision and the amount of laser energy needed to cut through the cornea.

(2) The second important type of laser-tissue interaction provided by the inventive system is area ablation, which permits direct sculpting of the corneal surface.

Figure 9A:
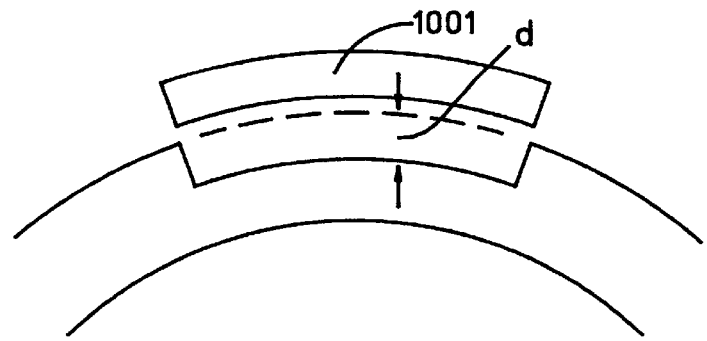
FIG. 9 is a cross-sectional side view of a cornea, showing the use of the present invention to remove tissue to a desired depth d over a predetermined area on the cornea, and showing an alternative method for performing a cornea transplant.

As illustrated in FIG. 9A, a local scar or infected tissue can be removed with the present invention. The defective tissue is removed to a desired depth d over a predetermined area on the cornea. A donor cornea cap 1001 can be cut and ablated ("sculpted") to the desired dimension, curvature, and thickness using the invention described in co-pending U.S. patent application Ser. No. 07/788,424. The cap piece is then transferred to the bared stroma bed and attached by suture, glue, or other appropriate means, in known fashion. The cap may be prepared in advance with an appropriate refractive power in a fashion similar to a contact lens. Such a cap can be used to change the refractive power of the eye to correct myopia, hyperopia, or astigmatism (regular or irregular).

Figure 9B:
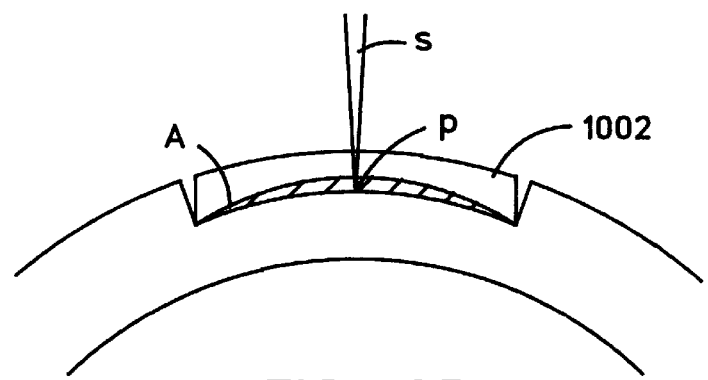

Referring to FIG. 9B, an alternative method is shown for performing a cornea transplant. Because the surgical laser beam S can be focussed through overlying tissue to an interaction point P, the surgical laser beam S can be used to ablate a layer of tissue beneath the surface of the eye to create an interior chamber A. Accordingly, using such "interior excision" or "intrastromal ablation", a section or segment of the cornea can be "excavated" in this manner, and then a circumferential ablation cut around the perimeter of the area can be made so that the entire segment can be lifted away from the eye as a cap 1002. If desired, the surgical laser beam S can be used to sculpt the back side of the material that will form the cap 1002, so as to change the refractive characteristics of the cap 1002. The cap 1002 can then be cut loose from the eye. If desired, further sculpting can be done directly on the exposed bed of the eye. Thereafter, the cap 1002 can be attached to the open ablated area by sutures or other known methods.

Another use of the invention is to produce standard or custom sculpted cornea caps in advance of need. The invention can be used on a donor cornea or a synthetic cornea substitute to ablate a desired profile to correct for myopia, hyperopia, or astigmatism. Such sculpted caps can then be attached to a properly prepared cornea, in known fashion.

Figure 10:
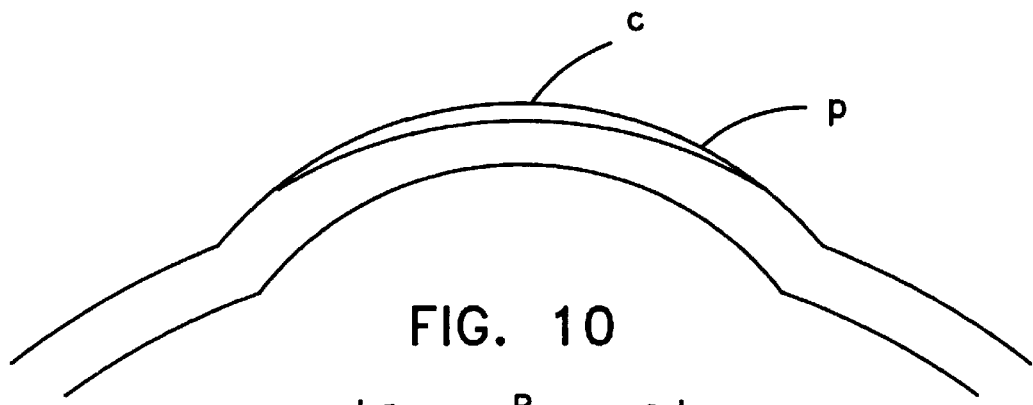
FIG. 10 is a cross-sectional side view of a cornea, showing the use of the present invention to correct myopia.

For myopia correction, as illustrated in FIG. 10, the curvature of the cornea can be reduced by selectively ablating the cornea such that more tissue is removed at the center portion C of the cornea, with a decreasing amount of tissue being removed towards the periphery P of the cornea. The inventive system can also be applied to ablate the corneal tissue near the surface of cornea. The new desired profile of the eye may include Bowman's membrane and part of the stromal layer, depending on the amount of refractive correction required. As described in co-pending U.S. patent application Ser. No. 07/788,424, the computer control unit 114 provides for the sequence, location, and intensity of laser pulses to be deposited. The deposition pattern is preferably in accordance with the patterns discussed in the section "Method of Depositing Laser Pulses" within the co-pending application.

Figure 12:
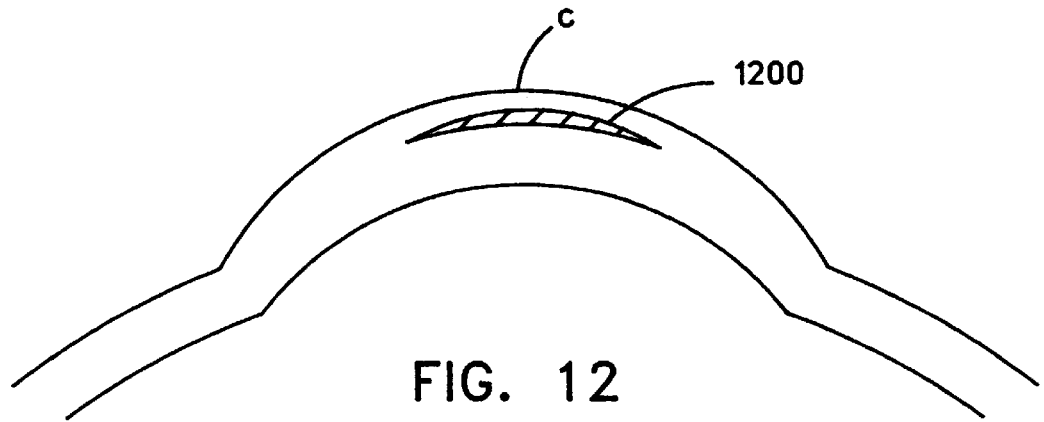
FIG. 12 is a cross-sectional side view of a cornea, showing the use of the present invention to correct myopia using an alternative method.

Another method for correcting myopia or hyperopia is to use the "interior excision" technique described above with respect to FIG. 9B. Referring to FIG. 12, correction of myopia may be performed by ablating material under the central portion C of the cornea. Depending on the amount of correction in the refractive power, the ablation gradient for the removed tissue varies. As the material overlying the chamber 1200 relaxes, it will reattach to the bottom of the chamber, thus changing the curvature of the eye.

Figure 11:
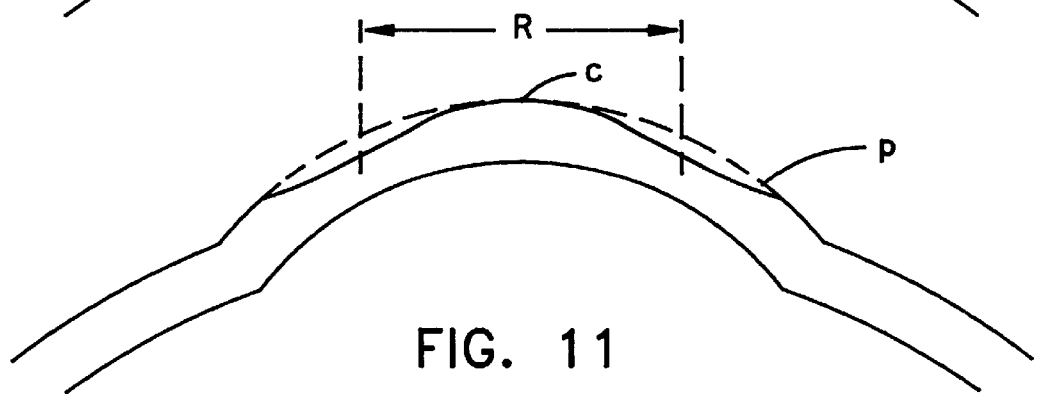
FIG. 11 is a cross-sectional side view of a cornea, showing the use of the present invention to correct hyperopia.

For hyperopia correction, as illustrated in FIG. 11, the objective is to increase the curvature of the eye. Cornea tissue is removed in an annular ring that is shallow near the center portion C of the cornea and increases in thickness towards the periphery P of the cornea. The depth of the removed tissue again decreases near the periphery of the eye for a smooth transition. Depending on the amount of correction in the refractive power, the etch gradient for the removed tissue varies. The size of the usable central region R varies depending on the amount of hyperopic correction.

Figure 13A:
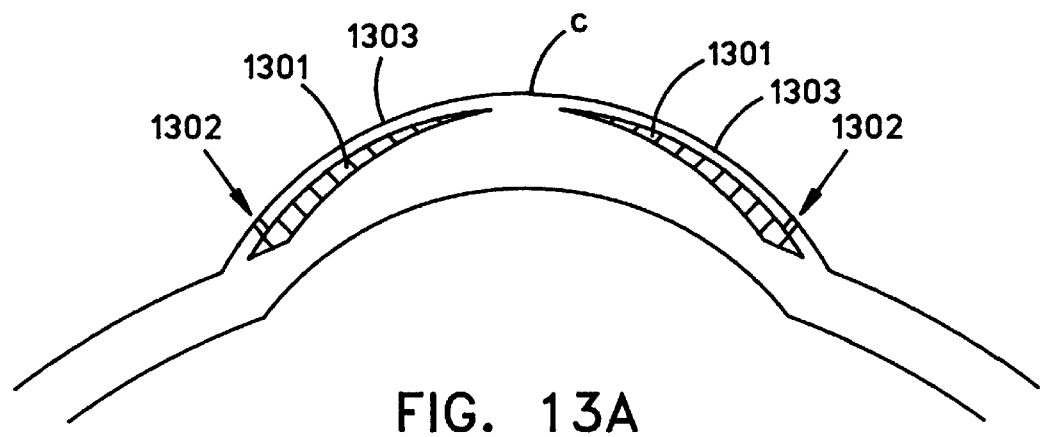
FIG. 13A is a cross-sectional side view of a cornea, showing the use of the present invention to correct hyperopia using an alternative method.
Figure 13B:
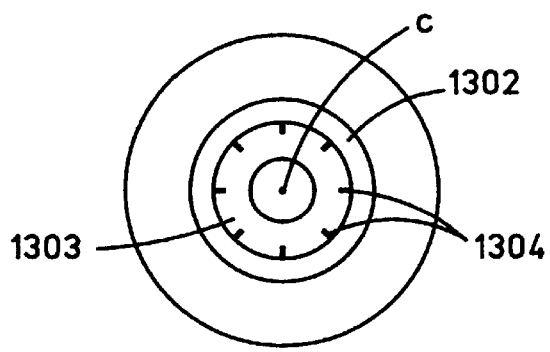
FIG. 13B is a top view of the cornea of FIG. 13A, showing the use of the perimeter radial cuts to help correct hyperopia.

Referring to FIG. 13A, hyperopia can also be corrected by ablating an annular chamber 1301 beneath the surface of the eye centered approximately on the center portion C of the cornea. Depending on the amount of correction in the refractive power, the ablation gradient for the removed tissue varies. After ablation of the chamber 1301, a circumferential excision 1302 is made around the bottom rim of the annular chamber 1301 to free an edge of the outer portion of the annular chamber 1301 from attachment to the eye, thereby creating a flap 1303. Generally, the flap 1303 will relax to the bottom of the chamber, thus changing the curvature of the eye. However, if the flap 1303 is not thin enough to so relax, small perimeter radial cuts 1304 (shown in FIG. 13B) may be made in the edge of the flap 1303 to further relax the flap and cause it to adhere to the bottom of the chamber 1301 formed by the interior excision.

In addition to the above methods for correction of myopia and hyperopia, the invention may be used to correct regular or irregular astigmatism, or complex refractive errors. The amount and distribution of tissue to be removed from various locations within the stroma is determined by the amount of correction required.

The invention is particularly useful for the correction of asymmetric refractive errors. Irregular distortions may result from poor matching of a cornea from a transplant, uneven suturing, or from imperfect refractive surgical procedures such as lamellar keratomileusis or epikeratophakia. The inventive system can direct the surgical laser beam to any desired location to sculpt the cornea according to a predetermined shape. The surgical laser beam thus can be applied to smooth out an irregular corneal profile.

(3) The third important type of laser interaction provided by the inventive system is intraocular excisions. The invention can be used to excise or photoablate regions within the cornea, capsule, lens, vitreoretinal membrane, and other structures within the eye.

For example, the present invention is useful for performing surgical procedures to correct glaucoma by creating a one or more openings through an iris to release fluids from the posterior chamber which create undesirable pressure behind the cornea. In addition, one or more excisions may be created in the posterior or anterior capsule to permit removal of material from the capsule and to implant an intraocular lens (IOL) or any other lens-like material or structure which can be in fluid or gel form. By directing the laser focus at the lens of the eye, a cataractal lens can be ablated and liquified. Thus, the inventive procedure can be used prior to an IOL implant for cataract conditioning. Furthermore, portions of the retinal membrane which create tension on the retina may be cut to relieve such tension. Also, portions of the retina may be operated upon to remove harmful tissue. Accordingly, the invention precisely controls and determines the location of the interaction point of a surgical laser beam, and controls the shape of the cornea during ophthalmic surgery.

Additional Embodiment

Another embodiment of a ophthalmic surgical laser system which can be adapted for use with the present invention to provide for precisely controlling and determining the location of the interaction point of a surgical laser beam, and for controlling the shape of the cornea during ophthalmic surgery, is set forth in co-pending U.S. patent application Ser. No. 07/967,253, entitled "METHOD AND APPARATUS FOR OPHTHALMIC SURGERY" and assigned to the assignee of the present invention. In that embodiment, a transparent applanator plate is placed in contact with the cornea of a patient's eye. The applanator plate creates a fixed positional frame of reference from which a laser beam control system can determine the desired point or points at which to focus the surgical laser beam, and thereby direct an interaction point of the beam to very precisely defined locations within the patient's eye. The surface of the applanator plate in contact with the patient's eye can be planar, concave, or convex, with either a spheric or aspheric curvature, a compound curve, or any other shape chosen by the surgeon. Applying the applanator plate to the cornea of the patient's eye causes the cornea to conform to the shape of the applanator plate.

Figure 14A:
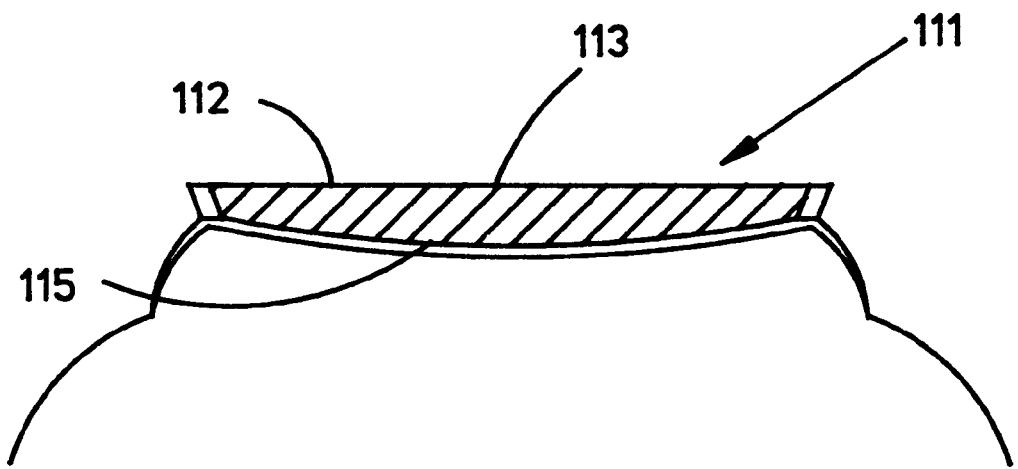
FIG. 14A is a cross-sectional side view of a convex applanator plate applied to an eye.
Figure 14B:
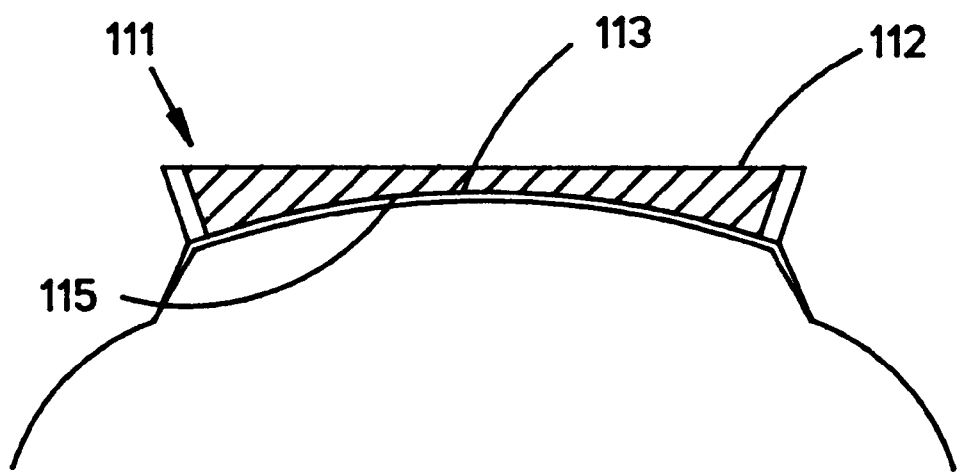
FIG. 14B is a cross-sectional side view of a concave applanator plate applied to an eye.

For example, FIG. 14A shows a cross-sectional side view of a convex applanator plate 111. The applanator plate 111 has at least two surfaces, a tip surface 112 and a corneal surface 113. The applanator plate 111 is placed in contact with the corneal epithelium 115 and deforms the cornea to conform to the convex shape of the corneal surface 113. As another example, FIG. 14B shows a cross-sectional side view of a concave applanator plate 111 applied to an eye. The applanator plate 111 is placed in contact with the corneal epithelium 115 and deforms the cornea to conform to the concave shape of the corneal surface 113.

A surgical tip at the distal end of an articulated arm having flexible joints is placed in contact with the tip surface 112 of the applanator plate 111 and follows any motion of the patient's eye. The articulated arm is coupled to a surgical laser source including a laser beam control system, such as the system described in co-pending patent applications filed by the present inventor for inventions entitled "Two Dimensional Scanner-Amplifier Laser" (U.S. patent application Ser. No. 07/740,004), and "Method of, and Apparatus for, Surgery of the Cornea" (U.S. application Ser. No. 07/788, 424). The surgical laser source also includes the source of the laser beam. The articulated arm directs the laser beam to the surgical tip, translating the motion of the beam relative to a reference frame fixed to the surgical laser source to a reference frame fixed with respect to the applanator plate to which the surgical tip is in contact. Since the shape of the cornea conforms to the contour of corneal surface 113 of the applanator plate 111, incisions of various shapes can be made by selecting an appropriate applanator plate and controlling the surgical beam to move linearly with respect to the fixed frame by the applanator plate.

The applanator plate 111 also provides a means to control the contour of the index of refraction boundary between the corneal epithelium 115 of the patient's eye and the air. Controlling the contour of this boundary reduces the distortion of the surgical laser beam which would otherwise be present due to the curvature of the outer surface of the epithelium and the difference in the index of refraction between the air and the stroma underlying the epithelium. The index of refraction of the applanator plate is preferably closely matched to the index of refraction of the cornea (i.e., index of approximately 1.38). The tip surface 112 of the applanator plate 111 is selectively shaped to provide a desirable contour at the boundary between the index of refraction of the stroma and air.

Thus, the applanator plate 111 serves at least three purposes: (1) to provide a positional reference for a surgical laser; (2) to control the shape of the patient's cornea during a surgical laser procedure; and (3) to provide a boundary between the epithelium and air, the contour of which can be controlled to reduce the distortion of the surgical laser beam. When used with the present invention, the applanator plate 111 provides even greater control of tissue removal.

Summary

In summary, the preferred method of performing a surface ablation of cornea tissue or other organic materials uses a laser source which has the characteristics of providing a shallow ablation depth or region (about 0.2 $\mu$m to about 5.0 $\mu$m), a low ablation energy density threshold (about 0.2 to 5 $\mu$J/(10 $\mu$m)$^2$, and extremely short laser pulses (having a duration of about 0.01 picoseconds to about 2 picoseconds per pulse) to achieve precise control of tissue removal. The laser beam cross-sectional area is preferably about 10 $\mu$m in diameter. The preferred laser system includes a broad gain bandwidth laser, such as Ti$_3$Al$_2$O$_3$, Cr:LiSrAlF$_6$, Nd:YLF, or similar lasers, with a preferred wavelength range of about 400 nm to about 1900 nm, which is generally transmissive in eye tissue.

Various surgical procedures can be performed to correct refractive errors or to treat eye diseases. The surgical beam can be directed to remove cornea tissue in a predetermined amount and at a predetermined location such that the cumulative effect is to remove defective or non-defective tissue, or to change the curvature of the cornea to achieve improved visual acuity. Excisions on the cornea can be make in any predetermined length and depth, and in straight line or in curved patterns. Alternatively, circumcisions of tissue can be made to remove an extended area, as in a cornea transplant. The invention can be used to excise or photoablate regions within the cornea, capsule, lens, vitreoretinal membrane, and other structures within the eye.

The present invention provides an improved method of eye surgery which has accurate control of tissue removal, flexibility of ablating tissue at any desired location with predetermined ablation depth, an optically smooth finished surface after the surgery, and a gentle surgical beam for laser ablation action.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

I claim:

1. A method for providing controlled ablation of organic material at a point of interaction by the steps of:
   (1) generating laser pulses having an energy density of less than 5 $\mu J/(10 \mu m)^2$ and a duration in a range of about 0.01 picoseconds to less than 1 picosecond;
   (2) applying the laser pulses to ablate organic material.

2. The method of claim 1, wherein the step of generating beam pulses includes generating at least one laser pulse having a wavelength transmissive in organic material.

3. The method of claim 1, wherein the step of generating beam pulses includes generating laser pulses emitted at a rate of up to approximately 100,000 pulses per second.

4. The method of claim 1, wherein the step of generating includes generating at least one laser pulse having been generated by a broad gain bandwidth laser.

5. The method of claim 1, including the further step of positioning the laser pulses within a selected portion of the material.

6. The method of claim 1, including the further step of determining the position of the laser pulses within the material.

7. The method of claim 1, including the further step of controlling the diameter of the cross sectional area of the laser pulses.

8. The method of claim 1, including the further step of determining the diameter of the cross sectional area of the laser pulses.

9. The method of claim 1, including the further step of controlling the intensity of the laser pulses.

10. The method of claim 1, including the further step of determining the intensity of the laser pulses.

11. The method of claim 1, including the further step of controllably blocking the laser pulses from the material.

12. The method of claim 1, wherein the step of generating beam pulses includes generating at least one laser pulse having a wavelength transmissive in eye tissue.

13. The method of claim 12, wherein the step of generating beam pulses includes generating laser pulses having a wavelength in one of the ranges of about 400 nm to about 1900 nm, about 2.1 to about 2.8 $\mu m$, or longer than about 3.1 $\mu m$.

14. The method of claim 1, including the further step of focusing the laser pulses at a selected interaction point in the material.

15. The method of claim 14, wherein the step of applying includes applying the laser pulses to a selected interaction point which has a diameter in the range of about 1 $\mu m$ to about 30 $\mu m$.

16. A method for ablation of eye tissue by the steps of:
   (1) generating laser pulses having an energy density of less than 5 $\mu J/(10 \mu m)^2$ and a duration in a range of about 0.01 picoseconds to less than 1 picosecond;
   (2) applying the laser pulses to ablate eye tissue.

17. The method of claim 16, further including the steps of:
   (1) positioning the laser pulses within a selected region of the eye tissue;
   (2) controlling the diameter of the cross sectional area of the laser pulses;
   (3) controlling the intensity of the laser pulses.

18. The method of claim 16, including the further step of controllably blocking the laser pulses from the eye tissue.

19. The method of claim 16, wherein the laser pulses have an undeflected position, and further including the step of generating a visible guide beam coaxial with the undeflected position of the laser pulses for aligning the laser pulses on an eye.

20. The method of claim 16, wherein the laser pulses have an undeflected position, further including the step of biasing the alignment of the undeflected position of the laser pulse with respect to the eye by tracking movement of the eye.

21. The method of claim 16, including the further step of using the laser pulses to make excisions on the exterior of the eye.

22. The method of claim 16, including the further step of using the laser pulses to make excisions within the interior of the eye.

23. The method of claim 16, including the further step of performing an ophthalmic surgical procedure for correcting myopia using the generated laser pulses, wherein the ophthalmic surgical procedure comprises the step of using the laser pulses to ablate an interior chamber beneath the central surface of the eye.

24. The method of claim 16, including the further step of performing an ophthalmic surgical procedure using the generated laser pulses, wherein the ophthalmic surgical procedure is selected from the group consisting of:
   (1) radial keratotomy;
   (2) creating transverse cuts in the cornea;
   (3) creating straight line excisions in the cornea;
   (4) creating curved-line excisions in the cornea;
   (5) creating multiple radial cuts, equal or partially equal in excision length and with an angular separation between cuts, made on the cornea;
   (6) creating a curved channel excision in the cornea;
   (7) creating a point excision in the cornea;
   (8) creating an interrupted line excision in the cornea;
   (9) creating a curved excision of varying depth in the cornea;
   (10) removing a geometric area from the cornea;
   (11) creating a spiral excision in the cornea;
   (12) creating holes in the posterior capsule of the eye;
   (13) creating holes in the anterior capsule of the eye;
   (14) creating holes in the iris;
   (15) cutting vitreoretinal membranes;
   (16) producing sculpted cornea caps in advance of need;
   (17) sculpting the cornea according to a predetermined shape;
   (18) removing cornea tissue in an annular ring around the center of the cornea;
   (19) removing cornea tissue such that more tissue is removed at the center portion of the cornea, with a decreasing amount of tissue being removed towards the periphery of the cornea; and
   (20) removing eye tissue.

25. The method of claim 16, including the further step of performing an ophthalmic surgical procedure for correcting hyperopia using the generated laser pulses, wherein the ophthalmic surgical procedure comprises the steps of:
   (1) using the laser pulses to ablate an interior annular chamber beneath the central surface of the eye;
   (2) using the laser pulses to make an annular excision near the periphery of the annular chamber to free an edge of the outer portion of the annular chamber from attachment to the eye.

26. The method of claim 25, wherein the ophthalmic surgical procedure comprises the further step of making perimeter radial cuts in the edge of the outer portion of the annular chamber.

27. A method of modifying the refractive power of the eye by the steps of:

(1) generating a laser beam comprising pulses having an energy density of less than 5 $\mu J/(10\,\mu m)^2$ and a duration in a range of about 0.01 picoseconds to less than 1 picosecond;

(2) applying the laser beam to ablate cornea tissue.

28. The method of claim 27, including the further step of removing a geometric volume of eye tissue inside the stroma or the Bowman's layer of the eye, thereby creating at least one cavity in the eye tissue.

29. The method of claim 28, including the further step of performing incisions of the cornea such that the portion of cornea locating above such cavities relaxes, collapsing the cavity such that the curvature of the eye at and near the optical axis of the eye is modified to attain a predetermined refractive power.

30. The method of claim 29, wherein the incisions are performed with either a laser or a mechanical instrument.

31. The method of claim 30, wherein the incisions consist of arcuate cuts shaped as predetermined arc lengths having a radius of curvature, positioned at predetermined locations from the visual axis of the eye.

32. The method of claim 30, wherein the incisions consist of radial cuts of predetermined lengths and depths, positioned at predetermined locations from the visual axis of the eye.

33. The method of claim 27, further including the steps of:

(1) applanating the cornea with an applanation plate such that (a) the location of the applanating plate provides a fixed three dimensional reference to the location of the laser beam, and (b) the shape of the cornea in contact with the applanation plate is conformed to a predetermined shape of the contact surface of the applanation plate;

(2) locating an interaction point of the laser beam inside the eye using the applanation plate as a location reference; and (3) ablating eye tissue of a predetermined shape.

34. The method of claim 33, wherein the predetermined shape can be any of a line, a geometric area, or a geometric volume.

35. The method of claim 33, wherein the contact surface of the applanator plate can be any of plano, concave, or convex.

36. The method of claim 35, wherein the step of generating includes generating at least one laser pulse generated by a laser medium selected from one of the $Ti^3:Al_2O_3$, $Cr:LiSrAlF_6$, and $Nd:YLF$.

\* \* \* \* \*